US011337955B2

(12) United States Patent
Emerson

(10) Patent No.: US 11,337,955 B2
(45) Date of Patent: *May 24, 2022

(54) COMPOSITIONS AND METHODS TO REGULATE HORMONAL CASCADES IN STRESS DISORDERS

(71) Applicant: BIOMMUNITY, INC., Bellevue, WA (US)

(72) Inventor: Paul G. Emerson, Bellevue, WA (US)

(73) Assignee: BIOMMUNITY, INC., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/807,659

(22) Filed: Mar. 3, 2020

(65) Prior Publication Data

US 2020/0197363 A1    Jun. 25, 2020

Related U.S. Application Data

(62) Division of application No. 15/993,576, filed on May 30, 2018, now Pat. No. 10,588,890.

(60) Provisional application No. 62/512,713, filed on May 30, 2017.

(51) Int. Cl.
| *A61K 31/353* | (2006.01) |
| *A61K 31/381* | (2006.01) |
| *A61K 31/198* | (2006.01) |
| *A61P 5/00* | (2006.01) |
| *A61P 25/28* | (2006.01) |
| *A61P 25/00* | (2006.01) |
| *A61P 9/12* | (2006.01) |
| *A61P 25/30* | (2006.01) |
| *A61P 25/02* | (2006.01) |

(52) U.S. Cl.
CPC .......... *A61K 31/353* (2013.01); *A61K 31/198* (2013.01); *A61K 31/381* (2013.01); *A61P 5/00* (2018.01); *A61P 9/12* (2018.01); *A61P 25/00* (2018.01); *A61P 25/02* (2018.01); *A61P 25/28* (2018.01); *A61P 25/30* (2018.01)

(58) Field of Classification Search
CPC .. A61K 31/198; A61K 31/353; A61K 31/381; A61P 25/00; A61P 25/02; A61P 25/28; A61P 25/30; A61P 5/00; A61P 9/12
See application file for complete search history.

(56) References Cited

U.S. PATENT DOCUMENTS

| 6,500,965 | B2 | 12/2002 | Paracchini | |
| 2002/0016478 | A1* | 2/2002 | Paracchini | A61K 36/48 |
| | | | | 549/403 |
| 2006/0257502 | A1* | 11/2006 | Liu | A61K 31/51 |
| | | | | 424/682 |
| 2007/0087063 | A1* | 4/2007 | Bland | A61K 31/59 |
| | | | | 424/729 |
| 2007/0292536 | A1* | 12/2007 | Kellermann | A61K 31/685 |
| | | | | 424/725 |
| 2009/0292021 | A1 | 11/2009 | Picaud et al. | |
| 2011/0064712 | A1* | 3/2011 | Amato | A61K 31/7076 |
| | | | | 424/94.2 |
| 2011/0236358 | A1* | 9/2011 | Sala | A61P 17/00 |
| | | | | 424/93.44 |
| 2012/0302942 | A1 | 11/2012 | Dipierro et al. | |
| 2013/0034537 | A1* | 2/2013 | Gocan | A61K 31/352 |
| | | | | 424/115 |
| 2015/0175645 | A1 | 6/2015 | Milburn et al. | |

FOREIGN PATENT DOCUMENTS

| EP | 1502597 | B1 | 5/2006 | |
| EP | 1854486 | A2 * | 11/2007 | ......... G01N 33/9413 |
| EP | 2018849 | A1 | 6/2011 | |

OTHER PUBLICATIONS

"GAPDH Glyceraldehyde-3-phosphate dehydrogenase", National Center for Biotechnology Information, U.S. National Library of Medicine, Bethesda MD, USA, Mar. 12, 2019, pp. 1-13.
"International Search Report and Written Opinion, PCT/US2018/035227", dated Aug. 27, 2018.
Baker, Ann E., et al., "Estrogen Modulates Microglial Inflammatory Mediator Production via Interactions with Estrogen Receptor B", Endocrinology 145(11), 2004, pp. 5021-5032.
Bazzichi, et al., "Exploring the abyss of fibromyalgia biomarkers", Clinical and Experimental Rheumatology, 28 (Suppl. 63), 2010, S125-S130.

(Continued)

*Primary Examiner* — Umamaheswari Ramachandran
(74) *Attorney, Agent, or Firm* — Kurt T. Muiville; VLP Law Group, LLP

(57) ABSTRACT

The invention is composition and methods that restore balance to the stress-related steroidal hormone cascade. Upon co-administration, the compounds of the invention restore balance to the cascade and promote or restore normal function in patients suffering from a disorder having a primary psychological stress component. The compositions include a selected combination of isoflavones, alpha lipoic acid, and L dopamine or a precursor thereof, and are preferably obtained from the natural sources disclosed herein. The uses of the invention include administration of the disclosed compositions to patients suffering from PTSD, fibromyalgia, endometriosis, and other disorders having a common chronic stress component.

12 Claims, 6 Drawing Sheets

(56) References Cited

OTHER PUBLICATIONS

Brignac-Huber, Lauren M., et al., "Cytochrome P450 Organization and Function Are Modulated by Endoplasmic Reticulum Phospholipid Heterogeneity", Drug Metabolism and Disposition, vol. 44, No. 12, Dec. 2016, pp. 1859-1866.
Carlson, David A., et al., "The plasma pharmacokinetics of R-(+)-lipoic acid administered as sodium R-(+)-lipoate to healthy human subjects", Alternative Medicine Review, vol. 12, No. 3, Sep. 2007, pp. 343-351.
Desantana , et al., "Animal models of fibromyalgia", Arthritis Research & Therapy, 15:222, 2013, 1-13.
Dunlop , et al., "The Role of Dopamine in the Pathophysiology of Depression", Arch Gen Psychiatry, vol. 64, Mar. 2007, 327-337.
Forster, Gina L., et al., "Revisiting the Role of the Amygdala in Posttraumatic Stress Disorder", The Amygdala—Where Emotions Shape Perception, Learning and Memories, Barbara Ferry, IntechOpen, DOI: 10.5772/67585., Jul. 5, 2017.
Fritz, Heidi, et al., "Soy, red clover, and isoflavones and breast cancer: a systematic review", PLOS One, vol. 8, Issue 11, Nov. 2013, pp. 1-18.
Georgakilas, Alexandros G., et al., "p21: A Two-Faced Genome Guardian", Trends in Molecular Medicine, vol. 23, No. 4, Apr. 2017, pp. 310-319.
Gocan , et al., "Balancing Steroidal Hormone Cascase in Treatment Resistant Veteran Soldiers Suffering from PTSD by a Fermented Soy Product (FSWW08) Improves Mental Symptoms and Immunity: A Pilot Study", The Vienna Stress Relief Clinic, Vienna Austria, BIOFOCUS, Rechlinghausen, Germany and Institute for Medical Research and Education, Essen, Germany., 1-36.
Gola , et al., "Posttraumatic stress disorder is associated with an enhanced spontaneous production of pro-inflammatory cytokines by peripheral blood mononuclear cells", BMC Psychiatry, 13:40, 2013, 8 pages.
Goslin , et al., "Prolonged Stabilization of Amyotrophic Lateral Sclerosis (ALS) with a Specially Fermented Soy Product (FSWW08): Case Report", Journal of Nutritional Therapeutics, vol. 2, 2013, 8-21.
Goswami, et al., "Animal models of post-traumatic stress disorder: face validity", Frontiers in Neuroscience, vol. 7, Article 89, 2013, 1.
Haaker , et al., "Single dose of L-dopa makes extinction memories context-independent and prevents the return of fear", PNAS on-line, Jun. 10, 2013, E2428-E2536.
Holman , et al., "A randomized, double-blind, placebo-controlled trial of pramipexole, a dopamine agonist, in patients with fibromyalgia receiving concomitant medications", Arthritis Rheum 52, doi:10.1002/art.21191, 2005, 2495-2505.
Holman, Andrew J., et al., "A Randomized, Double-Blind, Placebo-Controlled Trial of Pramipexole, a Dopamine Agonist, in Patients With Fibromyalgia Receiving Concomitant Medications", Arthritis & Rheumatism, vol. 52, No. 8, Aug. 2005, pp. 2495-2505.
Howes , et al., "Long-Term Pharmacokinetics of an Extract of Isoflavones from Red Clover (*Trifolium pratense*)", The Journal of Alternative and Complementary Medicine vol. 8, No. 2, 2002, 135-142.
Hwang, Ji-Sun , et al., "A dopamine-alpha-lipoic acid hybridization compound and its acetylated form inhibit LPS-mediated inflammation", European Journal of Pharmacology, vol. 746, Jan. 5, 2015, pp. 41-49.

Kalisch , et al., "L-dopa medication could be helpful in the treatment of phobias and post-traumatic stress disorder", Johannes Gutenberg—Universität Mainz (Press Release), Jul. 9, 2014.
Kang , et al., "Peripheral Biomarker Candidates of Posttraumatic Stress Disorder", Experimental Neurobiology, 24(3), 2015, 186-196.
Li, Shang , et al., "Formononetin promotes angiogenesis through the estrogen receptor alpha-enhanced ROCK pathway", Sci Rep. 2015; 5: 16815, Nov. 16, 2015, pp. 1-17.
Maron , "Damage to Pea-Size Gland May Cause PTSD-Like Symptoms", Scientific America, 2016.
Mesiano, Sam , et al., "Phytoestrogens Alter Adrenocortical Function: Genistein and Daidzein Suppress Glucocorticoid and Stimulate Androgen Production by Cultured Adrenal Cortical Cells", The Journal of Clinical Endocrinology & Metabolism, vol. 84, Issue 7, Jul. 1, 1999, pp. 2443-2448.
Navarro, Arturo Anadon, et al., "Report of the Scientific Committee of the Spanish Agency for Consumer Affairs, Food Safety and Nutrition (AECOSAN) on the risk of the use of seeds of Mucuna pruriens in craft products", Revista del Comite Cientifico de la AECOSAN, No. 24,, Jul. 13, 2016, 35-52.
Paradkar , et al., "Dietary isoflavones suppress endotoxin-induced inflammatory reaction in liver and intestine", Cancer Letters, vol. 215, Issue 1 (abstract), Nov. 8, 2004, 21-28.
Raczka, et al., "Empirical support for an involvement of the mesostriatal dopamine system in human fear extinction", Translational Psychiatry vol. 1, Jun. 7, 2011, 1-8.
Rajesh, R. , et al., "The Effect of Mucuna Pruriens Seed Extract on Pancreas and Liver of Diabetic Wistar Rats", Int J Cur Res Rev, vol. 8, Issue 4, Feb. 2016, pp. 61-67.
Rimessi, et al., "Mitochondrial reactive oxygen species and inflammation: Molecular mechanisms, diseases and promising therapies", The International Journal of Biochemistry & Cell Biology, 81, 2016, 281-293.
Rucci, Nadia , "Molecular biology of bone remodelling", Clinical Cases in Mineral and Bone Metabolism; 5(1), 2008, pp. 49-56.
Scotti Elena, et al., "Peroxisome Proliferator-Activated Receptor γ Dances with Different Partners in Macrophage and Adipocyte", Mol Cell Biol. vol. 30, No. 9., May 2010, pp. 2076-2077.
Shay, Kate Peterson, et al., "Alpha-lipoic acid as a dietary supplement: molecular mechanisms and therapeutic potential", Biochim Biophys Acta 1790 (10), Oct. 2009, pp. 1-31.
Singh, Krishna Bhan, et al., "Formononetin, a methoxy isoflavone, enhances bone regeneration in a mouse model of cortical bone defect", British Journal of Nutrition, 117, 2017, pp. 1511-1522.
Stephens, Mary Ann C., et al., "Stress and the HPA Axis: Role of Glucocoricoids in Alcohol Dependence", Alcohol Research: Current Reviews, 34(4), 2012, pp. 468-483.
Wang, Stephen W.J., et al., "Variable Isoflavone Contents of Red Clover Products Affect Intestinal Disposition of Biochanin A, Formononetin, Genistein and Daidzein", J Altern Complement Med., 14(Apr. 30, 2008, pp. 287-297.
Wu , et al., "Genistein alleviates anxiety-like behaviors in post-traumatic stress disorder model through enhancing serotonergic transmission in the amygdala", Psychiatry Res.,255 (abstract), Sep. 2017, 287-291.
Xu, Tai-Wiang , et al., "D1 and D2 dopamine receptors in separate circuits cooperate to drive associative long-term potentiation in the prefrontal cortex", PNAS, vol. 107, No. 37, Sep. 14, 2010, pp. 16366-16371.
Yehuda , et al., "Post-traumatic stress disorder", Nature Reviews—Disease Primers, vol. 1, 2015, 1-22.

\* cited by examiner

COMPOSITIONS AND METHODS TO REGULATE HORMONAL CASCADES IN STRESS DISORDERS

CROSS REFERENCE TO RELATED APPLICATIONS

This application is a divisional of U.S. patent application Ser. No. 15/993,576, filed May 30, 2018, U.S. Pat. No. 10,588,890, issued Mar. 17, 2020, and claims priority to U.S. Provisional Application 62/512,713, filed May 30, 2017. The priority of these applications is expressly claimed, and the disclosure is hereby incorporated by reference in their entirety.

BACKGROUND

People suffering from a large number of diseases experience chronic psychological stress that disrupts normal metabolic, hormonal, and steroidal processes. Abnormal metabolic, hormonal, and steroidal profiles are characteristically different from those of both non-stressed individuals and otherwise healthy individuals exposed to mental and physical stresses-even if those stresses are severe. In healthy individuals, stresses are mediated via a complex and interconnected human steroidal hormone cascade, and the natural response to these stresses is manifested as temporarily increased or decreased levels of certain hormones throughout the cascade. Temporary increases and decreases are a normal and healthy response that restores balance to the entire cascade. In healthy individuals, temporary increases and decreases in certain hormonal levels, often referred to as "up regulation" and "down regulation" successfully restores balance to the hormonal cascade and a normal and natural restoration of the cascade is a hallmark of a healthy response to both mental and physical stress.

Even when stress is extreme, short term stresses, typically measured in terms of hours to days, in healthy individuals illicit a reliable and appropriate hormonal cascade response to counteract the stresses. This normal and healthy response is measurably and fundamentally different than the response exhibited by patients suffering from chronic mental stress. For example, elite soldiers subjected to extreme survival training exercises involving starvation and sleep deprivation during survival training regimens exhibit temporary and increases or up regulation of anti-inflammatory hormones in the upper level of the hormonal cascade, down regulation of estradiol in addition to testosterone and temporary suppression of the immune system is observed although also reversed in the short to intermediate term.

In contrast, some individuals who suffer from chronic psychological physical stress exhibit massive and sustained disruptions in the entirety of the hormonal cascade that is unique and characterized by widespread up regulation of hormones at the "top" of the cascade—hormones that are well recognized as related to stress and anxiety. Hormones at the "bottom" of the cascade, known to be critical to cellular immunity, and are required for protection from infection, inflammation, allergies, protection from cardiovascular disease, healthy barrier function, and cell repair, are dramatically reduced or down-regulated across the entire cascade.

Moreover, the specific hormonal imbalances between the anxiety hormones at the upper portion of the cascade and the immune-protective hormones at the bottom of the cascade is characteristic chronic stress disorders and causes an entire range of comorbidities, including tendency to physical accidents, depression, hyperlipidemia, atherosclerosis, by failure of the immune system, suicide, and an overall significant and measurable reduction in life expectancy. These comorbidities are not seen in healthy individuals whose hormone cascade exhibits a natural and normal response to stress.

As an example, the normal up-regulation of cortisol in response to severe short-term stress performs a valuable function by reducing inflammation. However, in abnormal chronic stress conditions, cortisol is down regulated in response to chronic emotional or psychological stress. The healthy up-regulation of cortisol beneficially stimulates the immune system whereas the abnormal down regulation leads to dangerous comorbidities including hypertension, increases in cholesterol and triglycerides, increased susceptibility to viruses and other pathogens, joint pain, gastrointestinal disorders, increased cancer risk, increased food and other allergies, increased G.I. disease, and an increased risk of autoimmune disease.

Significant hormone imbalances are seen most typically in conditions that, contrary to short-term physical and mental stresses, involve permanent and continuous exposure to stress that has a primary psychological component, even though physical stresses may also be present. Although the causes, progression, the physical symptoms of these diseases can vary greatly, the common component is continuous and significant psychological stress that unbalances the hormonal cascade resulting in increase in the entire range of anti-inflammatory hormones and a decrease in the immune protective components. Thus, although chronic stress disease conditions such as severe mental disease, post-traumatic stress disorder, schizophrenia, bipolar disease, and other chronic conditions have a wide range of underlying causes and impact dramatically different patient populations, each is accompanied by an identifiable stress response in the human steroidal hormone cascade. Also, in these afflicted populations, the characteristic stress responses have no tendency to normalize over time and display a broad-based shift in hormonal values across the cascade that is abnormal and causes a broad range of other pathologies and comorbidities.

Severe mental diseases (including Post Traumatic Stress Disorder (PTSD), schizophrenia, bipolar disorder) are accompanied by co-morbidities including systemic pain, hyperarousal, depression, insomnia, and cognitive and behavioral abnormalities. Patients suffering from severe mental diseases in chronic stress exhibit an abnormal lipid profile that leads to increased risk of stroke and heart attack, increased risk of immune disorders, metabolic syndrome, and systemic inflammation, inflammatory bowel diseases, atherosclerosis, viral and bacterial infections.

Although chronic, untreated stress disorders have a variety of treatment options, including drugs and psychological counseling, none of the existing treatments address the characteristic and chronic imbalance in the steroidal hormone cascade. While individual elements of the cascade have been addressed by prior treatments, no known attempts have yielded a unified, yet multi-faceted approach to re-balancing the hormonal cascade, especially by reversing the global up regulation of the production of hormones at the top of the cascade and global down-regulation of hormones at the bottom of the cascade Therefore, a need exists for new formulations and medicinal compositions and disease-specific methods of treatment that promote re-balancing of the human steroidal hormonal cascade to counteract the abnormal up-regulation of certain selected hormones and the abnormal down-regulation of other hormones. Counteracting this imbalance will reduce the adverse effects of the chronic distortion of the hormonal cascade and by restoring healthy hormonal balance, ameliorate the symptoms caused by the imbalance, including reduction of the direct symptoms of stress-related disorders, both psychological and physical, and including the related comorbidities.

SUMMARY OF THE INVENTION

Aberrations in the hormonal cascade are counteracted by administering a combination of compounds that influence hormone regulation, synthesis, and metabolism and promote restoration of overall balance in the steroidal hormonal cascade. Although the range of conditions exhibiting aberrant hormonal values are varied, and the specific alterations in aberrant hormonal values compared to normal can be different, the invention normalizes aberrant hormonal values, regardless of the quantitative differences in the specific abnormalities, and restores a more normal balance in the hormone cascade.

The pharmaceutical compositions of the invention include components that provide a synergistic effect in restoring balance to the hormone cascade. By co-administering these compositions, abnormally reduced or down regulated levels of selected steroidal hormones can be increased by metabolizing existing precursors to these compounds. Also. the abnormal decrease or down regulation of other hormones and selected precursor hormones is alleviated by administering precursors that increase biosynthesis and concentrations of compounds that are downstream in the hormonal cascade. For example, the decrease of precursor hormones (for example DHEA and pregnenalone) leads to increased biosynthesis of testosterone, the adiols, estradiol, estradiol metabolites, and cortisol.

A first component is a specially selected combination of isoflavones that shift the steroidal cascade away from corticosterone and toward the "adiols," (androstenediol, aldosterone, androstenetriol, androstanediol, estradiol, 2-OH-Estradiol, and 2-Methoxy-Estradiol) and testosterone. Preferably, the combination of isoflavones is obtained from a specific natural source that yields a preferred relative and absolute concentrations between and among specific isoflavones species, specifically between and among four individual isoflavones and most specifically having minimum concentrations of two specific isoflavones that have cooperative metabolic effects to achieve the goal of restoring hormonal balance. Specifically, the natural source isoflavone preferably comprises at least formononetin and biochanin A, and preferably also further comprises genistein, and daidzein.

The isoflavone component of the composition may also contain other constituent components that indicate that the source of selected isoflavones is naturally derived. These can include other chemical compounds identified in naturally sourced isoflavones, or plant materials that are characteristic of the isoflavone source. A particularly preferred source of the selected isoflavones is the plant commonly known as Red Clover (Trifolium pratense) and is comprised of four preferred isoflavones formononetin, biochanin A, genistein and diadzein in desirable ratios and concentrations and other trace elements, such as plant matter consistent with the Red Clover source. These isoflavones are also anti-inflammatory and tend to couple to the same receptor sites as anti-inflammatory hormones in the cascade, thereby reducing the need for endogenous biosynthesis, and allowing a shift in hormonal synthesis away from these hormones toward the lower end of the steroidal hormone cascade. Other sources of each of the preferred isoflavones are known, and chemical synthesis of each compound disclosed herein is possible, although for economic reasons and the balance of constituent compounds, the Red Clover natural source is preferred.

A second component is pharmaceutical grade alpha-lipoic acid administered in a selected form that has high potency and physiological availability. Specifically, the preferred form of alpha lipoic acid is highly enriched in the (R+) enantiomer (RLA) and acts as a cofactor for enzyme complexes. The preferred formulation is substantially free of the (L) enantiomer, at a minimum, has smaller percentage of the (L) enantiomer compared to the (R) enantiomer. A particularly preferred source is an enhanced RLA having increased bioavailability, limited inactive components, and at least 85-90% of the R-enantiomer.

The third component is L-dopamine or a precursor of L-dopamine (L-3,4-dihydroxyphenylalanine) specially selected for bioactivity and is preferably derived from a natural source. Preferably, the source is naturally derived from *Mucuna pruriens* extract that contains L-dopa. In the presence of the other constituents of the compositions of the invention, L dopamine has several beneficial effects on restoration of balance to the human steroidal hormonal cascade. Catechol-O-methyltransferase (COMT) catabolizes L-dopa and degrades estradiol. *Mucuna Pruriens* also provides a bioavailable L-dopa precursor that is metabolized to yield measurable increases, or preservation of nominally normal, concentrations of estradiol in vivo. Estradiol is a precursor of 2-methoxy estradiol (2-ME), regulates blood pressure blood pressure and acts as a neuroprotective agent.

The methods of the invention include treatment methods for a group of conditions characterized by persistent abnormalities in the human steroidal hormone cascade. The methods include co-administration of the compositions described herein, as well as formulation of the disclosed compositions using selected ingredients, co-factors, excipients, and precursors. The methods include targeted alterations to the human steroidal hormone cascade including down regulation, or reductions in in vivo concentrations of at least cholesterol and corticosterone and reduction in concentrations or activity of catechol-O-methyltransferase (COMT). The methods include up regulation, or increases in in vivo concentrations of at least the adiols, including specifically 2-methoxy-estradiol, androstenediol, androstenetriol, and androstanediol, and testosterone.

The methods also include providing the compositions of the invention to influence the in vivo concentration of hormonal precursors to alter aberrant hormonal cascades, to return the hormonal cascade to the "normal" state, and to mitigate the deleterious effects of aberrant hormonal shifts. The methods include methods of manufacturing the three-component composition of the invention including combining each of the proposed agreements in their preferred, most bioavailable and active forms, including finalizing a dosage form as any orally administered dosage format, preferably including pills, suspensions, capsules, liquids, emulsions, and dispersions. The methods include administration of selected dosage ranges of the three components of the invention in synergistic combination, and over a time profile determined to elicit cooperative absorption and in vivo activity of each elements The conditions subject to methods of administration of the present invention have a chronic stress-induced pathology characterized by a primary mental component. The methods of the invention include administering pharmaceutically active concentrations of the compositions described herein for treating each of Post Traumatic Stress Disorder (PTSD), fibromyalgia, high blood pressure, eclampsia, and preeclampsia, inflammatory bowel syndrome (IBS), depression, including post-partum depression, and unnatural cell growth. The methods also include reducing acute psychological stress that accompanies other physical and psychological disorders including mental disease, dementia, including particularly Lewy Body dementia, Parkinson's disease, and addiction withdrawal. The methods include administering the compositions of the invention together with other compounds administered for treatment of psychological stress or the underlying psychological or physical condition yielding the psychological stress. For example, treatments for high blood pressure or stress disorders frequently include other pharmaceutical compositions that are co-administered with the composition of the present invention. Within this context, co-administration means delivering both the compounds of the present invention together with another beneficial therapeutic compound such as both have simultaneous beneficial effects within the timeframe of administration of either compound.

Additionally, because of the stress reducing effect of the compositions of the present invention, the compounds described herein may be administered as part of a regimen to reduce use of another composition where phasing out, reducing, or eliminating use of the other composition is desired. For reduction of the effects of addiction, for example with substances of abuse, the compounds of the present invention can be administered as part of a tapering regimen such that administration of the other compound or substance of abuse is reduced over time together with coadministration of the compounds described herein.

Synergism between the individual elements of the compounds of the invention allows relatively reduced concentrations or dosages of any individual component to be administered while still producing therapeutic effects. For example, earlier dosages of isoflavones have been reported at ranges between 700 mg two 1500 mg without significant effect across the entire range of stress-induced disorders. Compositions pursuant to the invention, involving isoflavones in combination with L-dopa, and L-dopa precursors, together with R+lipoic acid significantly reduce the concentration the isoflavone compounds that must be administered for efficacy.

Any or all of the three-component composition may be formulated in a sustained release format that alters the pharmacological profile of absorption and metabolism depending on the underlying indication as described below. Timing of administration includes conforming the concentration or dosage of the administered compositions for an area-under-curve (AUC) pharmacological model or a peak $C_{MAX}$ concentration model wherein the combination of concentrations and dosages is pharmaceutically active.

As will be described in more detail below, special selection of the source and composition of the at least three individual components of the pharmaceutical compositions of the invention yields important benefits in bioavailability, potency, efficacy, and tolerability. Moreover, use of the specially selected sources and compositions yields a dose that is tolerable and readily administered to a human patient as part of an ordinary lifestyle and diet plan.

As disclosed in more detail below, preferred embodiments of the invention feature specific selected absolute and relative concentrations of and ratios between the minimal three components of the pharmaceutical combination as well as selected ratios between two of the three, and three of the three components of the invention. Balancing the ratios and compositions of the individual components enhances the ability of the compositions of the invention to restore the steroidal hormonal cascade towards a more normal balance.

Although the individual indications may vary according to the source of the stress in the underlying disease, the preferred embodiments have ranges of individual concentrations and ratios among the components that exhibit synergy among the individual components when administered to a patient in need thereof. Because the hormonal cascade is, as seen in the accompanying Figures, a complicated and highly dependent web of chemical reactions, minimum concentrations and an overall balance balancing between the individual compositions of the invention produces a more preferred systemic result.

The compositions of the invention are tailored for oral administration in a dosage form that is well tolerated, and it does not result in gastrointestinal distress or interfere with other medications used to treat stress disorders or their co-morbidities.

BRIEF DESCRIPTION OF THE DRAWINGS

FIGS. 1A-1D are a hormonal cascade showing the progression of up regulation and down regulation across normal to stress-induced conditions. FIG. 1 A is a representation of the basic hormonal cascade with the anti-anxiety hormones shown in the "top" of the cascade and the immune and cardioprotective hormones shown in the "bottom" of the cascade. FIG. 1B shows both up and down regulation in well-trained marathon runners. FIG. 1C shows both up and down regulation in elite soldiers undergoing extreme physical stress and starvation in survival training. FIG. 1D shows up and down regulation in severe mental disease.

DETAILD DESCRIPTION OF THE INVENTION

Definitions:

The terms "therapeutically effective amount," as used herein, refer to a concentration or dosage of a compound sufficient to treat, ameliorate, or prevent the identified disease or condition, or to exhibit a detectable therapeutic, prophylactic, or inhibitory effect when administered to a human suffering from a chronic stress disorder resulting in abnormalities in the human steroidal hormone cascade.

The effect of administration of a therapeutically effective amount of the compositions of the invention can be detected by measurement of in vivo concentrations of the components of the cascade graphically represented in FIG. 1, and including observable physiological parameters, for example, an improvement in an identified clinical condition, or reduction or absence of symptoms or reduction or absence of co-morbidities. The precise effective amount for a subject will depend upon the clinical condition, the subject's body weight, size, and health; the nature and extent of the condition; and the therapeutic or combination of therapeutics selected for administration along with the compositions of the invention.

As used herein, a patient "in need of steroid hormonal balance therapy" is a patient who would benefit from administration of the three constituents of compositions of the invention to alleviate a disorder characterized by chronic stress. The patient may be suffering from any disease or condition for which hormonal rebalancing therapy is a component of a therapeutically or physiologically beneficial response particularly where alleviation of stress disorders reduces or eliminates symptoms or co-morbidities.

The terms "co-administration" or "co-administered" means that the 3 components of the compositions of the invention are given to a patient in need of hormonal therapy balancing therapy at a concentration and at a dosage and over a time frame such that the compounds act synergistically and in vivo on the balance of compounds, relative ratios of compounds or metabolism of individual steps, or the entire hormonal cascade of FIGS. 1A-1D, preferably, coadministration of the compositions of the invention detectably alter metabolism of the stress response elements of the steroidal cascade.

Generally, the hormonal cascade of these conditions manifests themselves as an increase in the anti-inflammatory hormones, such as aldosterone and cortisol, and a reduction in the hormones at the "bottom" of the cascade, such as testosterone and estradiol. Thus, the preferred therapeutic effect is one that "unblocks" the "blockade" in the steroid hormonal cascade and allows hormonal flow away from the anti-inflammatory hormones and toward the aldiols (especially estradiol) and testosterone.

Figure 1A:
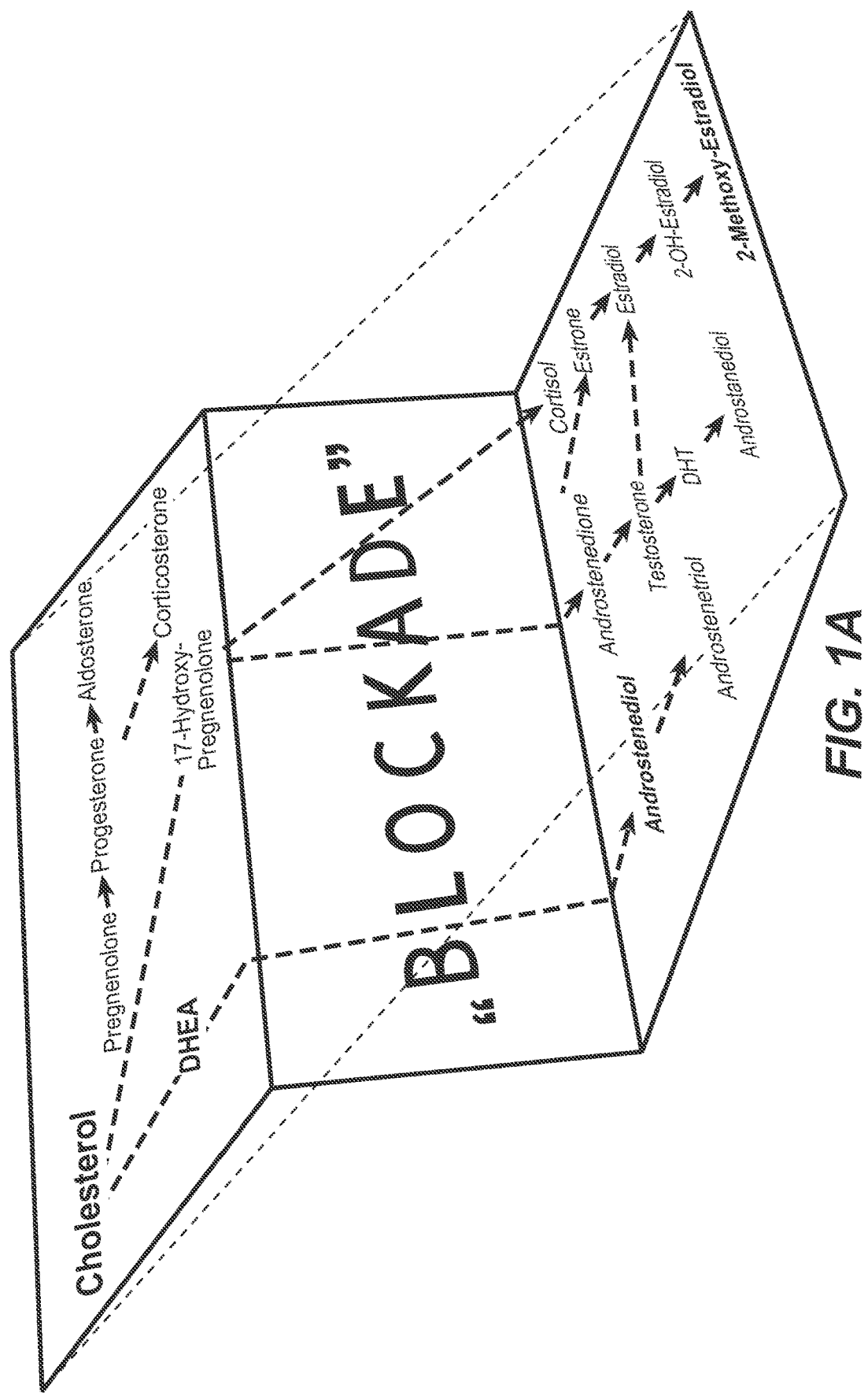
FIGS. 1A-1D.
Figure 1B:
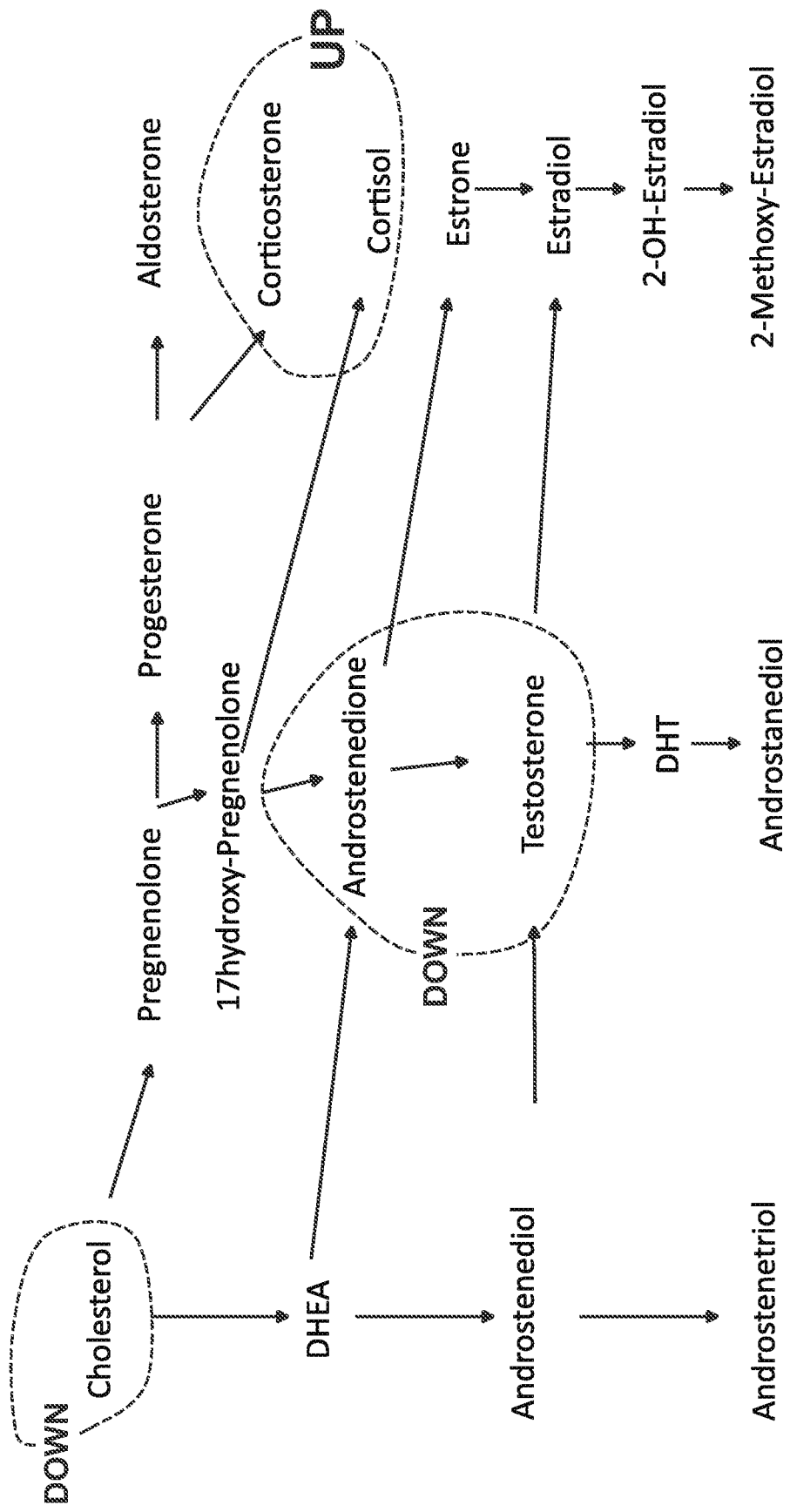
Figure 1C:
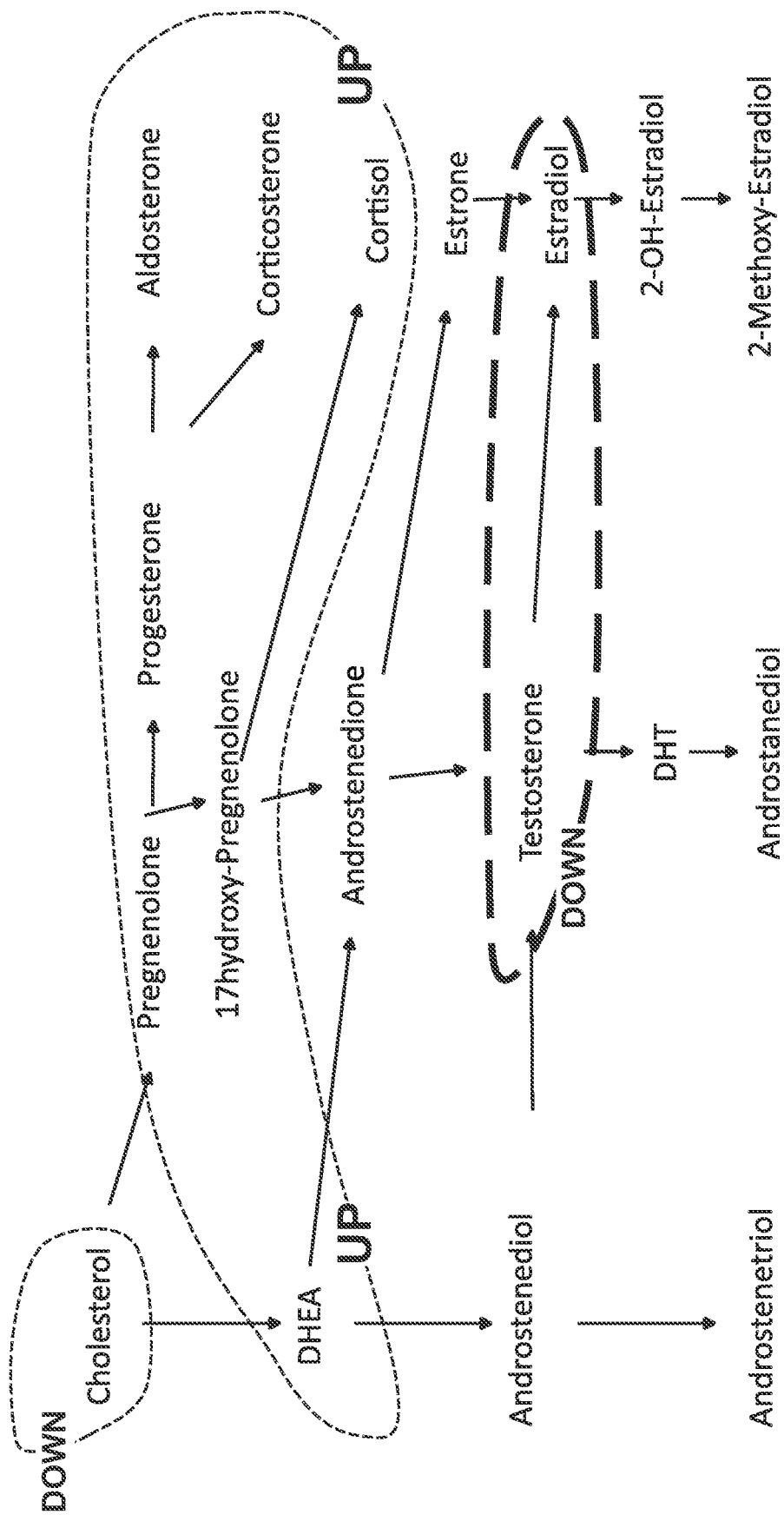
Figure 1D:
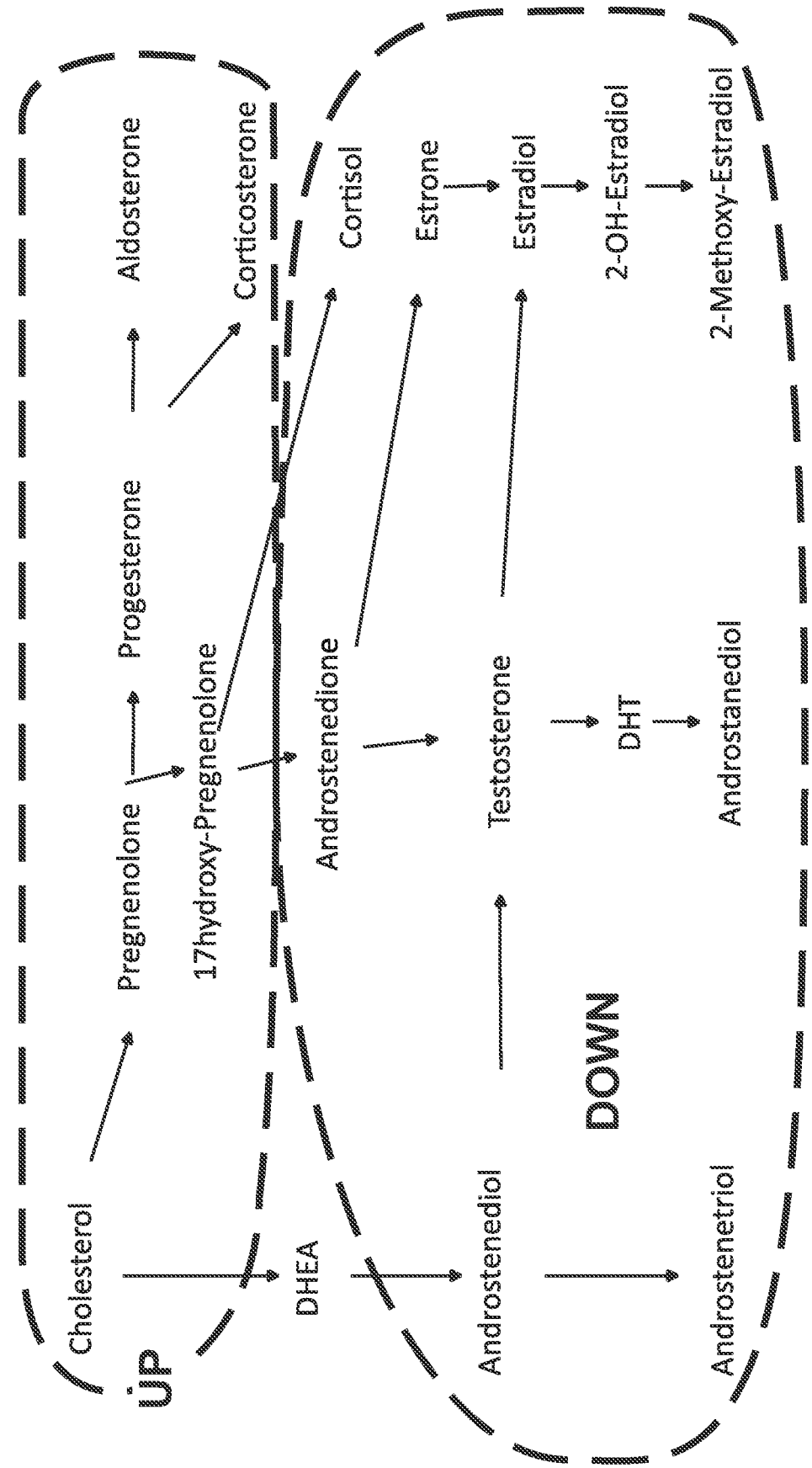
Figure 2:
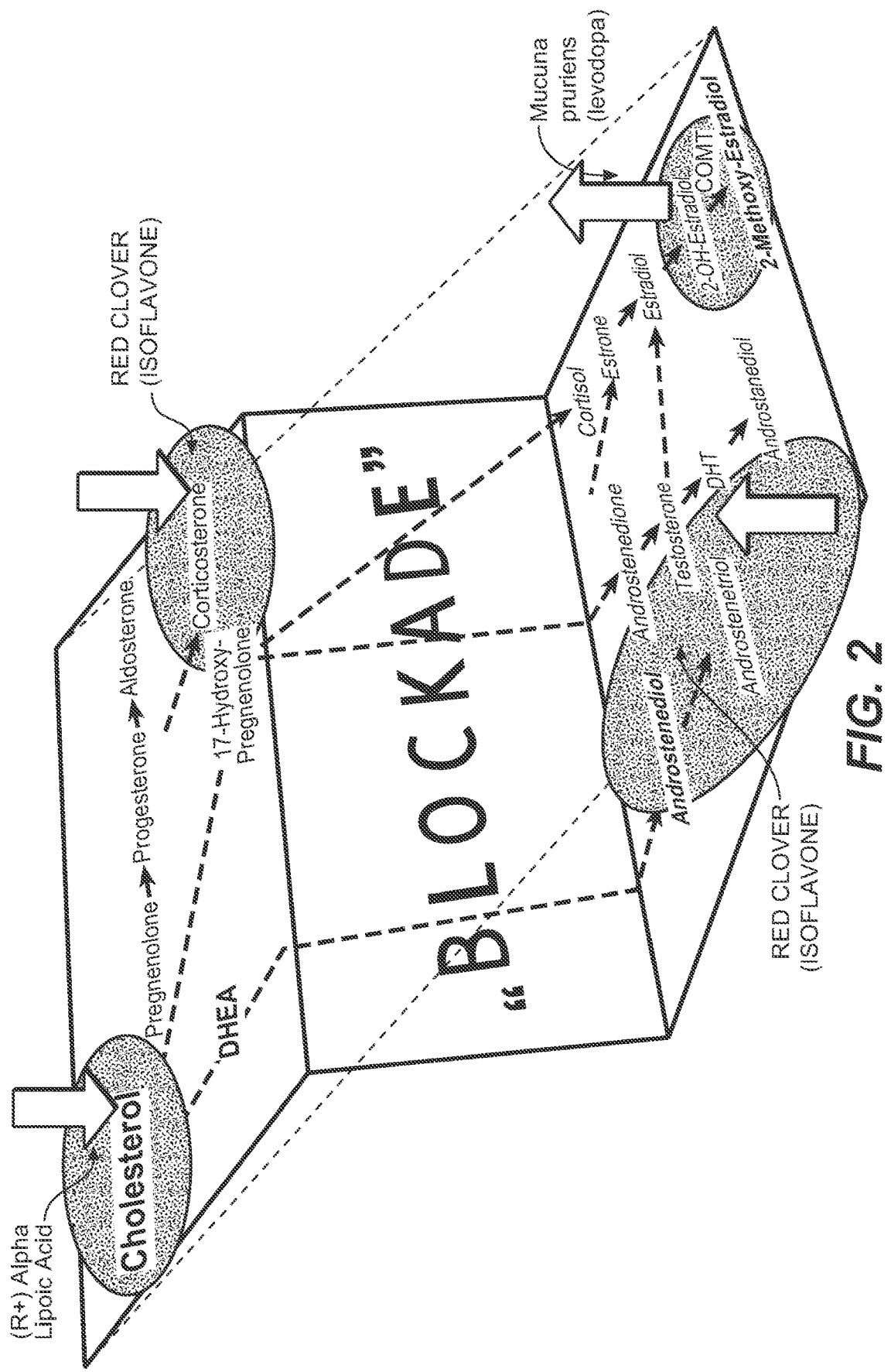
FIG. 2 shows the impact of the compositions and methods of the invention on the same human steroidal hormone cascade showing specifically selected up and down regulation of various components of the cascade to ameliorate a chronic stress condition having primarily a mental component thereof.

The physiological response to chronic stress having a primary mental component, as noted above, is fundamentally different in afflicted patients compared to healthy individuals. Referring to FIG. 1A-D, the characteristic steroidal hormone cascades seen in various stress-induced conditions including well-trained marathon runners (FIG. 1B), elite soldiers under survival conditions (FIG. 1C) severe mental disease like PTSD, schizophrenia, and bipolar disease (FIG. 1D) reflecting shifts in the hormonal cascade that are unique to normal conditions (FIGS. 1B and 1C). The differences show transient down regulation of cholesterol in normal response patients and up regulation in chronic stress conditions. Corticosteroid and cortisol are normally upregulated, whereas cortisol can be down regulated in chronic stress. A shift to increased production of DHEA, corticosterone and aldosterone at the "top" of the cascade is seen with elite soldiers (FIG. 1 C) which is eventually resolved to normal condition. These hormones are related to stress and anxiety. Referring to FIG. 1 D, because the precursors for estradiol and testosterone, and their metabolites, are decreased, those hormones at the "bottom" of the cascade, which are involved in immune protection (infection, inflammation, and allergies), cardiovascular disease protection, promotion of a healthy barrier function, and cell repair, are reduced. In addition to the loss of these critical functions, afflicted patients are subject to a range of other conditions and comorbidities that are detectable across populations of patients afflicted with conditions ranging from severe psychological disorders, post-traumatic stress disorder (PTSD), preeclampsia, fibromyalgia, and others.

Referring again to FIG. 1D, specifically with respect to patients with PTSD and severe mental disease, the decrease of loss of function in mechanisms of cellular and specific immunity result in an increased susceptibility to viral and bacterial infections, as well as a reduction in the capability of the immune system to respond to such infections. Attenuation of the immune response can lead to joint pain, stomach disorders, inappropriate allergic reactions and diffuse sensations of pain. In addition to the increased blood pressure experienced when estradiol is reduced, a decrease of estradiol may lead to detrimental effects in cell repair because the estradiol metabolite, 2-methoxyestradiol (2ME) plays a role in transforming stem cells into functional cells and decreases in 2ME are observed in eclampsia and preeclampsia.

The composition of the invention is a co-administered combination of α-lipoic acid, soluble red clover extract, and *Mucuna pruriens* extract, all of which are natural, have USP designations, and have established safety profiles for enteral administration at the levels proposed. The administration of this combination results in behavioral effects that include antistress, antianxiety, anti-depression, improved sleep, reduced blood pressure and general increases in patient reported quality of life. More generally, the compositions of the invention have therapeutic effect in reduction of distortion or moderation of stress pathways, including moderation or regulation of steroidal hormone metabolic pathways that are abnormally affected by chronic stress disorders.

The treatment effects include reduction of comorbidities including blood glucose disorders, infections, inflammations, and overall quality of life and life expectancy. The methods of the invention therefore include increasing the rate of treatment response and outcome success in patient populations suffering from a chronic stress disorder having a primarily mental component. Because the referred formulations of the invention are safely orally delivered, and are comprised of natural ingredients, the compositions of the invention can readily be combined with traditional medical, pharmaceutical treatments without contraindication. Accordingly, compositions of the invention include the specific formulations described herein when coadministered with tricyclic antidepressants, monoamine oxidase inhibitors, selective serotonin reuptake inhibitors, other verbal antidepressants, and any psychiatric medications, including but not limited to clozapine, olanzapine, and other second-generation antipsychotics.

While the compositions are preferably naturally sourced, and selected from the specific sources identified herein, all the compounds described herein can be artificially synthesized. Because the natural sources are preferred, the compositions of the invention include characteristic compositions of active ingredients selected from natural sources as well as byproducts, other active or inert ingredients, or any other chemical or biological signature that indicates a natural source of the active ingredient. Accordingly, while a completely synthetic version of the compositions disclosed herein would be efficacious, naturally sourced materials are preferred, and a feature of the invention is characteristic chemical profiles indicating natural sources for at least one individual ingredient.

The recommended daily therapeutic dose of the isoflavone components 75-600 mg, 100-500 mg, 200 to 350 mg, greater than 240 and greater than 300 mg of soluble red clover extract preferably comprising approximately 40% or greater of isoflavone constituents compounds in the natural source. Accordingly, in a 300 mg naturally derived isoflavone-containing Red Clover constituent, approximately 120-140 mg would be a combination of the four primary preferred isoflavone constituents.

For the alpha lipoic acid component, the recommended daily dose is 300-600 mg and preferably 200 to 2350 mg and most preferably approximately 225-275 mg α-Lipoic acid. As noted below, a preferred formulation includes at least 80%-90% enrichment of the (R) (+) enantiomer and is formulated as sodium salt.

L-dopamine from the plant species *Mucuna Pruriens* is present as a racemic mixture and, as noted herein, is preferably obtained as an extract of the natural product although synthetic approaches to the (L) enantiomer are readily available. The recommended daily dose is preferably 25 to 100 mg, more preferably 30 to 60 mg and most preferably 15-40 mg as provided by a 15% *Mucuna pruriens* extract yielding, depending on the potency, 2 mg-6 mg as a daily dose of active ingredient.

Example #1

Isoflavone Constituent—Sources, Preferred Forms, Dosages

As noted above, the isoflavones constituent is preferably naturally sourced, is aglyconated, separate from sugars in their natural glycosidic form, and may be obtained by fermentation or any form of extraction that yields the profile of the isoflavone constituent as described below. USP grade Red Clover extract is a preferred plant source, although a number of other plant species can provide sources of isoflavones, including but not limited to soybean (*glycine max L*), green bean (*Phaseolus vulgaris L.*), Alpha sprout (*Meicago satica L.*), mung bean sprouts, (*Vigna radiata L.*), cowpea (*Vigna unguiculata L.*), kudzu root (*Puerarya lobata L.*), and specifically red Clover Blossom and red clover sprout (*Trifolrum pratense L.*), or from faba beans.

Red clover is a perennial plant with trifoliate leaves and pink to red flowers. The plant derives its name in part from its flowers, which are fragrant and can range in color from white to a dark red. Red clover is a member of the legume family and has been used worldwide as a source of hay for cattle, horses and sheep and by humans as a source of protein in the leaves and young sprouts and is available over-the-counter as a non-specific medicinal for human use and is regarded as non-toxic in daily dosages of at least 300 mg/day.

Red Clover extract provides a source of each critical isoflavone employed to promote the shift in the human steroidal hormone cascade away from cortisone and aldosterone, and toward adiols, estradiol, and testosterone and have a profound beneficial effect on the steroidal pathway when administered as described herein and with the remaining active compounds described in the following Examples. Isoflavones are chemically similar in certain structural aspects to the important adiols. Without being bound to any theory of efficacy, preferred isoflavones can bind estrogen receptors (estrogen receptor β-agonists) throughout the body. Such an effect yields decreased levels and activity of cortisone and other anti-inflammatory hormones, resulting in an increase in preferred estrogen and androgen metabolites, such as adiols and testosterone.

Although isoflavones have been tested in some stress conditions, see e.g., Prolonged Stabilization of Amyotrophic Lateral Sclerosis (ALS) with a Specially Fermented Soy Product (FSWW08): Case Report, Journal of Nutritional Therapeutics, 2013, 2, 8-21, the isoflavone composition and relative ratios must be carefully formulated to maximize efficacy. The preferred red clover isoflavone sources provide threshold concentrations of specific key isoflavones, biochanin A and formononetin, as well as beneficial ratios of two other key isoflavones including genistein and diadzein. As shown in the data table below, Red Clover is particularly high in formononetin and biochanin A, which are the major constituents in the compositions of the invention, but which also include trace amounts of genistein and daidzein, which are beneficial but are necessary in lower concentrations and dosages. Accordingly, the invention includes, but is not limited to, compositions comprising formononetin and biochanin A as major constituents and the isoflavone combination. Individually, these two constituents, either individually or together may comprise at least 10%, 20%, 30%, 40%, 50%, 60%, 70%, 80%, or 90%, of the total isoflavone combination. Also, the relative ratio of formononetin: biochanin A range from 1:5 and encompass 1:4, 1:3, 1:2, 1:1, 2:1, 3:1, 4:1, and 5:1 and comprise specific values that distinguish a red clover source from a soy-source or other source that does not characteristically yield the above ratios in the aglyconated form.

The source of the isoflavone constituent used in manufacture of compositions of the invention must be carefully monitored for individual concentrations and relative concentrations and ratios of the preferred isoflavone species. For example, a comparison of selected contributions of individual isoflavones between soy and red clover in over-the-counter commercial sources readily illustrates the differences in concentrations.

| Isoflavone | Mg/Soy Sample | Mg/Red Clover Sample |
|---|---|---|
| Formononetin | 0.14 | 29.35 |
| Biochanin A | 0.00 | 14.47 |
| Genistein | 2.77 | 0.96 |
| Daidzein | 2.78 | 0.75 |

Andres et al. Determination of the isoflavone composition and estrogenic activity of commercial dietary supplements based on soy or red clover. Food Funct., 2015. 6:2017-2025. Accordingly, even if the total isoflavone content is approximately equal to the red clover natural source, a mismatch in the relative and absolute concentrations of the preferred isoflavone constituents can be significantly detrimental to efficacy. Moreover, natural sources of Red Clover are known to be highly variable in isoflavone concentrations even among the four preferred species See Variable Isoflavone Content of Red Clover Products Affects Intestinal Disposition of Biochanin A, Formononetin, Genistein, and Daidzein, J. J. Alt. Compl. Med. Volume 14, Number 3, 2008, pp. 287-297.

Figure 3:
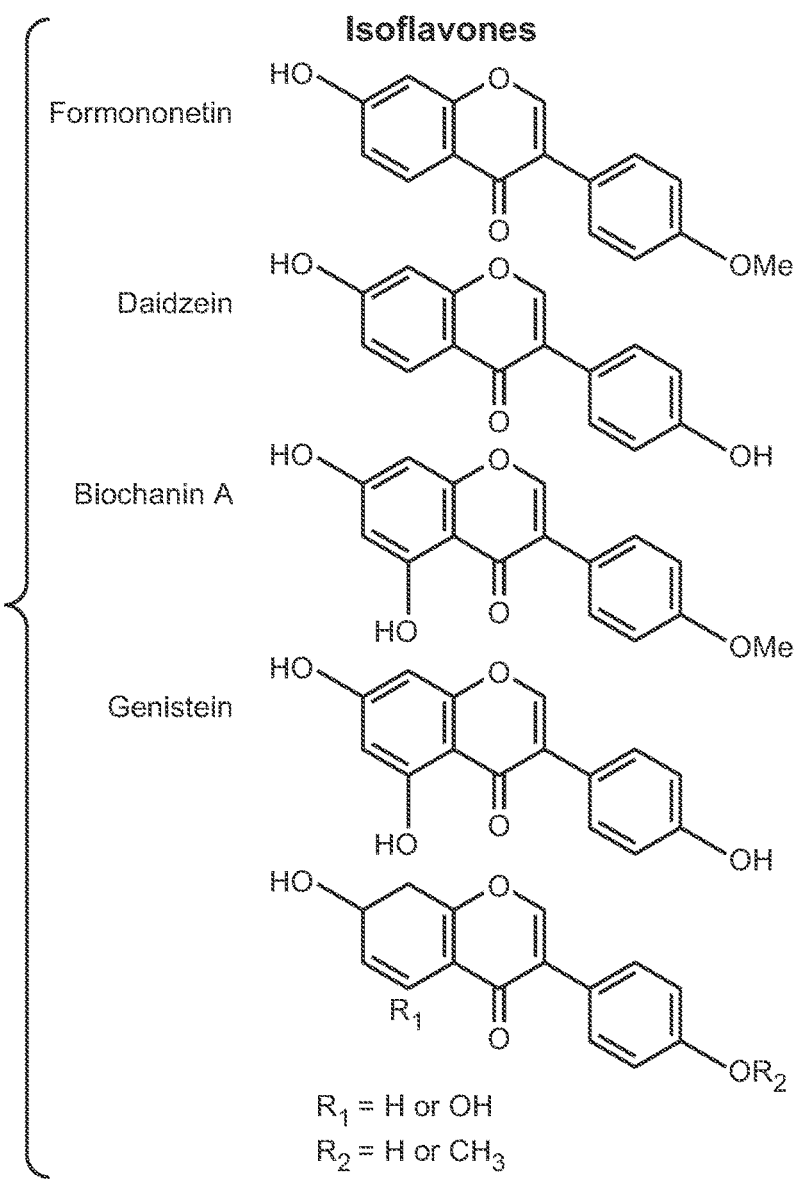
FIG. 3 is the chemical structures of four preferred isoflavones constituents in a preferred embodiment of the composition of the invention: formononetin, biochanin A, daidzein, and genistein and a generic isoflavone compound encompassing the selected isoflavone species.

In a preferred embodiment, the source of isoflavones is a red clover extract containing 40-50 mg isoflavones per tablet but can range to one hundred or 200 mg per tablet. This extract is a preferred source of the four major isoflavones it is provided under a COA designating a total isoflavone percentage of 39.7% comprised of the following: (biochanin A 19.4%, formononetin 19.4%, genistein 0.6%, and diadzein 0.3%). Referring to FIG. 3, the chemical structures of formononetin, biochanin A, diadzein, and genistein are illustrated together with a generic aglyconated isoflavone backbone having substitutions at $R_1$ and $R_2$ to yield the four preferred species. In a preferred formulation of the invention, the total isoflavone constituent is approximately 40% or greater of the total of the mixture. With biochanin A comprising proximally 16-22%, formononetin comprising proximally 16-22%, genistein comprising approximately 0.4-0.8% and diadzein comprising proximally 0.2-0.4%, with the substantial remainder of the material comprised of inert plant material that is characteristic of the Trifolium genus and specifically Trifolium pratense The material is produced by extracting isoflavones from red clover plant material by masquerading the plant material with water and an organic solvent to select at least 8% (w/w) of isoflavone constituents.

| Isoflavones constituent total daily dosage | Range 50-1400 mg | Preferred 200-500 |
|---|---|---|
| Biochanin A | 20-600 | 50-100 |
| Formononetin | 20-600 | 50-100 |
| Genistein | 5-100 | 10-40 |
| Diadzein | 5-100 | 10-40 |

Figure 4:
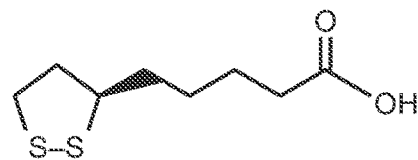
FIG. 4 is the chemical structure of the preferred enantiomer R(+) of alpha Lipoic acid (RLA).

Example 2

α-Lipoic Acid R(+) C$_8$H1402 (RLA)

α-Lipoic acid is known to increase cholesterol in stressed individuals, which in turn is converted to DHEA, adiols, and testosterone. Alpha lipoic acid has been studied for its role in energy metabolism and protection of intracellular damage from reactive oxygen species (ROS). Up-regulation, or preservation of in vivo concentrations of these compounds, promote normalization of the human steroidal hormone cascade. Alpha lipoic acid exhibits a synergistic effect with the selected isoflavone concentrations described in Example 1 above. Referring to FIG. 4, alpha lipoic acid is an organosulfur compound derived from octanoic and is normally present in eukaryotic cells and is necessary for aerobic metabolism. Alpha lipoic acid contains two sulfur atoms (C6, C8) connected by a disulfide bond in either sulfur atom can exist in higher oxidation states. The C6 carbon atom is chiral and two enantiomers of alpha lipoic exist (R)-(+) and (L)(−). For purposes of the present invention, alpha lipoic acid constituent that is highly enriched for the (R)-(+) enantiomer is preferred. In a particularly preferred formulation, a sodium salt of an (R) (+) enriched composition has increased bioavailability and solubility according to selected formulation parameters. The preferred lipoic acid concentration has at least 80%, and preferably at least 90%, total of the (R) (+) enantiomer and is relatively low (less than 2.0%) insoluble polymer. The raw composition contains 9 to 10% sodium and traces of carbonate and soluble polymers of the R-lipoic acid sodium salt. In vivo testing shows that a preferred formulation of R-lipoic acid described herein increases bioavailability and solubility. The preferred composition is substantially free of organic solvents, has a specific rotation [alpha]$_D$ 20=+60−+85, and a melting point of 240° to 250° centigrade with decomposition beginning at approximately 210° C. And a particle size less than forty mesh. During the formulation process, the favorable ratio of the (R) (+) enantiomer in the constituent is preserved by maintaining the heat less than 50° C.

As noted above, daily dosages of R-alpha lipoic acid are 300-600 mg and preferably 200 to 250 mg and most preferably approximately 225-275 mg α-Lipoic acid. And is enriched to at least 80%-90% of the (R) (+) enantiomer and is formulated as a sodium salt.

Example 3

L-DOPA (Mucuna ruriens)

Figure 5:
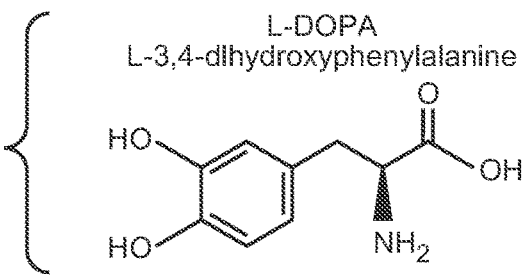
FIG. 5 is the chemical structure of 1-dopamine wherein the naturally occurring forms of L-dopamine or precursors thereof are preferred.

Referring to FIG. 5, Levodopa (L-DOPA) (L-3,4 dihydroxyphenylalanin-(S)-Amino, has been administered to address deficiency in the synthesis of the neurotransmitter dopamine in nerve cells. However, in contrast to dopamine, L-dopa can cross the hemaotencephalic (brain) barrier and enter nerve cells where it is to carboxylated to dopamine. L-dopa can also be oxidized toward melanin producing leucodopachrome and dopachrome by auto-oxidation or by reaction with tyrosineases (polyphenol oxidases).

Mucuna pruriens extract contains L-dopa, which has several direct actions on the hormonal cascade including causing increases to 2-methoxyestradiol (2ME) and decreases in COMT. COMT catabolizes L-dopa and degrades estradiol. Mucuna provides additional L-dopa so that estradiol can be preserved. Estradiol is a precursor of 2ME, which has several important physiological activities, including a reduction in blood pressure. L-dopa has been used as an anti-Parkinson's drug, thus indicating its role as a neuroprotective agent. Additionally, the bioactive peptides of Mucuna pruriens have been shown to have hypolipidemic and antithrombotic activity. L-Dopa is extracted from various mucuna seeds which have reported the yield of L-dopa as 1.9% where as simple hot water extraction methods are reported to give excellent recovery of L-Dopa (3.1-6.1%) from the seeds of nine species of mucuna genus. However, although the Mucuna genus is a preferred source of L-dopa, a variety of other species described in Table 1 below are natural sources of L-dopa.

Table 1: Plants reported to contain L-Dopa.

TABLE 1

Plants reported to contain L-Dopa

| Plant | Plant part | L-Dopa (%) |
|---|---|---|
| Alysicarpus rugosus. | Seed | 0.65 |
| Bauhinia purpurea. | Seed | 2.2 |
| Bauhinia racemosa | Seed | 0.73 |
| Canavalia ensiformis. | Seed | 2.46 |
| Canavalia gladiata. | Seed | 2.13 |
| Cassia floribunda | Seed | 1.1-1.9 |
| Cassia hirsute | Seed | 2.37-2.82 |
| Dalbergia retusa. | Seed | 2.2 |
| Glycine wightii. | Seed | 0.2 |
| Mucuna andreana | Seed (excluding seed coat) | 6.3-8.9 |
| Mucuna aterrima. | Seed | 3.31 |
| Mucuna aterrima. | Seed (black) | 4.2 |
| Mucuina birdwoodina tutcher | Seed | 9.1 |
| Mucuna ochinchinensis | Seed (ash) | 0.96-4.2 |
| Pericarp | Seed (ash) | 0.09-0.22 |
|  | Leaf (ash) | 0.18-1.35 |
|  | Stem (ash) | 0.28-0.31 |
|  | Root (ash) | 0.14-0.16 |
| Mucuna cochinensis | Seed | 3-4 |
| Mucuna deeringiana | Seed | 2.7-3.13 |
| Mucuna gigantean | Seed | 1.50-3.78 |
| Mucuna holtonii | Seed 14,13 | 6.13-7.5 |
| Mucuna monosperma | Seed | 4.24-4.56 |
| Mucuna mutisiana | Seed | 3.9-6.8 |
| Mucuna pruriens | Seed (excluding seed coat) | 5.9-6.4 |
| Mucuna pruriens | Seed | 1.25-9.16 |
| Mucuna pruriens | Seed (black) | 3.8 |
| Mucuna pruriens | Whole bean | 4.02 |
| Endocarp |  | 5.28 |
| Mucuna pruriens f. hirsute | Seed | 1.4-1.5 |
| Mucuna pruriens f. utilis | Seed | 1.8 |
| Mucuna pruriens var. utilis | White (Whole seed) | 4.96 |
| Mucuna pruriens var. utilizes | Seed (White) | 6.08 |
| Mucuna pruriens var. utilizes | Seed (spotted) | 3.6 |
| Mucuna sloanei | Seed | 3.34-9.0 |
| Mucuna urens | Seed | 4.92-7.4 |
| Parkinsonia aculeate | Seed | 0.64 |
| Phanera vahlii | Seed | 2.35 |
| Pileostigma malabarica | Seed | 2.13 |

TABLE 1-continued

Plants reported to contain L-Dopa

| Plant | Plant part | L-Dopa (%) |
|---|---|---|
| Prosopis chilensis | Seed | 1.25 |
| Vicia faba var minor | Dry seed | 0.07 |
|  | Green pods (whole unripe) | 0.60 |
|  | Green plant with pods | 0.56 |
|  | Green flowering plant | 0.40-0.46 |
|  | Green vegetative plant | 0.24-0.57 |
| Vicia narbonensis. | Green pods (peel only) | 0.5 |
|  | Green plant with pods | 0.6 |
| Vigna aconitifolia | Seed | 0.20 |
| Vigna unguiculata | Seed | 0.45 |
| Vigna vexillata | Seed | 0.52-0.58 |

Accordingly, the presence of L-dopa which was previously thought to be available only in *Mucuna* and Vicia is also isolated from many other plants beyond these two genera. Although, higher amount of L-dopa is noticed only in *Mucuna* species. Therefore, a systemic screening of these plants may provide an alternative to synthetic L-dopa opening new avenues for herbal cultivation and therapies. Dopamine can exist as a racemic mixture but is preferably isolated in a form that is substantially enriched for the L form. L dopamine from the plant species *Mucuna Pruriens* is present as a racemic mixture and, as noted herein, is preferably obtained as an extract of the natural product although synthetic approaches to the (L) enantiomer are readily available. The recommended daily dose is preferably 25 to 100 mg, more preferably 30 to 60 mg and most preferably 15-40 mg as provided by a 15% *Mucuna pruriens* extract yielding, depending on the potency, 2 mg-6 mg as a daily dose of active ingredient.

L-DOPA can be administered in combination with a peripheral decarboxylase inhibitor, such as carbidopa, to reduce the conversion of dopamine to its metabolic products. L-dopa may also be co-administered with vitamin B6.

Example 4

Combination of Three Elements and Synergy

Co-administration of the three active components described above, will restore the steroids to the preferred cascade. Co administration is defined as simultaneous administration of the three components of the invention within a time and at a concentration that yields a synergistic effect between at least two and preferably all three of the components. This includes a reduction in aldosterone and cortisone and an increase in estradiol, 2-methoxyestradiol (2ME), testosterone, and the potent immunoregulatory adiols (e.g. androstenediol). Concomitantly, COMT (Catechol-O-methyltransferase), an enzyme that degrades estradiol and the catecholamines (e.g. dopamine, epinephrine, and norepinephrine), is decreased.

Coadministration of the three compounds promotes hormonal balance, leading to a reduction or alleviation of the symptoms of the conditions described above, or may in fact, eliminate the condition itself. In the above figure, α-lipoic acid contributes to the synthesis of cholesterol, which is required for steroidal hormone synthesis. The addition of red clover's anti-inflammatory isoflavones, which couple to the same receptor sites as the anti-inflammatory hormones, will reduce the need for these hormones (e.g. such as aldosterone and cortisol), and thus allow a shift of the hormonal synthesis away from these hormones toward hormones in the lower end of the cascade. This shift also allows the immune system to "normalize," and with the increase in cholesterol, the hormonal cascade can synthesize the preferred hormones, such as the aldiols, testosterone, and estradiol.

The pharmaceutical composition of the present invention may further comprise at least one excipient selected from a diluent, a binder, a disintegrant, and a lubricant. Examples of the diluent may include microcrystalline cellulose, lactose, mannitol, calcium phosphate and the like; examples of the binder may include povidone, hydroxypropyl cellulose, hydroxypropyl methylcellulose, polyvinyl alcohol, sodium carboxymethyl cellulose and the like; examples of the disintegrant may include crospovidone, sodium croscarmellose, sodium starch glycolate and the like; and examples of the lubricant may include magnesium stearate, calcium stearate, sodium stearyl fumarate and the like.

Preferably, the diluent may be used in an amount ranging from 20 to 80% by weight, the binder may be used in an amount ranging from 1 to 10% by weight, the disintegrant may be used in an amount ranging from 1 to 30% by weight and the lubricant may be used in an amount ranging from 0.5 to 5% by weight, based on the total weight of the composition.

The pharmaceutical composition of the present invention can be formulated for oral administration. Representative examples of the formulation for oral administration may include powders, a tablet, a capsule, granules or syrup, preferably a tablet or capsule, but are not limited thereto.

The pharmaceutical composition of the present invention may be coated with a coating substrate to prevent the composition from being contact with hand or skin of a user. The coating substrate employed in the present invention may include a rapid release coating substrate such as hydroxypropyl cellulose, hydroxypropyl methylcellulose, polyvinyl alcohol, polyvinyl alcohol-polyethylene glycol graft polymer (Kollocoat IR, BASF) and the like; an enteric coating substrate such as (metha)acrylate copolymer (Eudragit, EVONIK), hydroxypropyl methylcellulose phthalate, cellulose acetate phthalate and the like; and a sustained release coating substrate such as cellulose acetate, ethyl cellulose, polyvinyl acetate and the like. The coating substrate may be used in an amount ranging from 1 to 50% by weight, preferably 1 to 30% by weight, based on the uncoated core.

Example 5

Endometriosis and Related Conditions

Endometriosis, secondary amenorrhea, and abnormal uterine bleeding, in the absence of organic pathology, such as submucous fibroids or uterine cancer, are due to hormonal imbalance. The conditions are marked by pain and uterine bleeding. Present treatments, none of which are completely effective, include the administration of female hormones, norethindrone acetate and progestin. The methods of the present invention include administration of the composition defined herein for the treatment of endometriosis in a patient in need thereof.

Example 6

Fibromyalgia

Fibromyalgia is a disorder characterized by widespread musculoskeletal pain accompanied by fatigue, sleep, memory and mood issues. Researchers believe that fibromyalgia amplifies painful sensations by affecting the way the brain processes pain signals. Symptoms sometimes begin after a physical trauma, surgery, infection or significant psychological stress. In other cases, symptoms gradually accumulate over time with no single triggering event. The methods of the present invention include administration of the composition defined herein for the treatment of fibromyalgia in a patient in need thereof.

Example 7

Severe Mental Disease and Post Traumatic Stress Disorder

Although the physical basis of severe mental disease and disorders such as PTSD are not thoroughly understood, both conditions can result from acute or mild traumatic brain injury or repeated concussion. PTSD is typically regarded as an interaction between the subject, a traumatic event, and social contexts that causes the physical stress component to persist as a chronic condition resulting from the mental stress component. PTSD has been observed to have a profound effect on immunity and inflammatory disorders and a strong correlation exists between the onset of PTSD and SMD-related stress with immune system dysfunction and chronic diseases containing an inflammatory component. Although the comorbidities of both PTSD and SMD have been noted, no unified treatment exists. Accordingly, the method of the invention includes administering a therapeutically effective amount of the compositions of the invention to a patient in need thereof.

Individuals may develop PTSD after being exposed to a traumatic event such as combat experiences, a motor vehicle crash, or sexual assault. Symptoms of PTSD may include nightmares, intrusive thoughts, or other re-experiencing phenomena, the avoidance of situations that remind the person of the traumatic event, a feeling of numbness or being socially detached from family and friends, and hyper-arousal (for example, feeling angry, irritable and "on edge," or having difficulty concentrating). Hyper-arousal or hyper-vigilance includes a rapid and pronounced reaction to stressors which may lead to a preoccupation with signs of threat and emotional distress. Persons with PTSD may have other challenges such as difficulties with employment, relationships, or other health conditions (for example, depression, alcohol abuse or drug dependency).

Example 8

Cardiac Function and Hypertension

Disruption of the steroidal hormone cascade leads to several discrete cardiovascular comorbidities. Chronic stress has been observed to contribute to acute and chronic diseases including but not limited to atherosclerosis, hypertension, persistent high blood pressure, vascular disorders, and increase in vascular rigidity. The methods of the invention include administering the compositions described herein to a patient in need of therapeutic intervention for cardiovascular disorders resulting from chronic psychological stress.

Example 9

Substance Abuse and Remediation

Chronic stress is both a cause and a result of substance abuse, withdrawal, and a permanent distortion of the steroidal hormone cascade is a potential long-term effect of substance abuse. The method of the invention includes delivering a therapeutically effective amount of the compositions described herein to a person suffering from substance abuse, undergoing withdrawal, or employing a taper strategy to reduce the harm associated with long-term substance abuse. In the methodology of the invention, direct therapeutic administration of the compositions of the invention can be applied both to reduce the chronic stress that leads to the compulsion to self-administer addictive substances, to reduce the stress associated with withdrawal or tapered-lessening of the use of addictive substances, or the direct reduction in the stress-induced comorbidities resulting from short and long-term substance abuse.

Example 10

Stress-Accompanied Dementia

The umbrella term dementia includes several disorders having different physiology's, such as Alzheimer's disease, Lewy body dementia, and other forms of pathologies characterized by long-term cognitive decline. Research studies have discovered that chronic such as psychological stress, even suffered in mid-life, can contribute to the deterioration of mental function accompanied by any of the disorders probably characterized as dementia. The administration of the compositions of the invention serves both to reduce the stress-induced physiological events that lead to cognitive decline, as well as reducing the comorbidities that accompany the stress resulting from loss of mental function by afflicted patients.

The Examples disclosed above are merely intended to illustrate the various utilities of this invention. It is understood that numerous modifications and variations of the present invention are possible considering the above teachings and, therefore, within the scope of the appended claims, the present invention may be practiced otherwise than as particularly disclosed.

All patents and publications are herein incorporated for reference to the same extent as if each individual publication was specifically and individually indicated to be incorporated by reference. It should be understood that although the present invention has been specifically disclosed by preferred embodiments and optional features, modification and variation of the concepts herein disclosed may be resorted by those skilled in the art, and that such modifications and variations are considered to be within the scope of this invention.

What is claimed is:

1. A synergistic composition consisting essentially of the three active agents in a physiologically active dose of:
   (1) an R(+) enantiomer of alpha-lipoic acid;
   (2) L-dopamine derived from *Mucuna* genus; and
   (3) a combination of two or more of isoflavones having the formula:

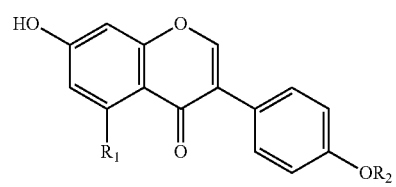

$R_1$ = H or OH
$R_2$ = H or $CH_3$ wherein R1=H and R2=CH3 and R1=OH and R2=CH3 are at least 30% of a total isoflavone dosage and are present in a ratio between 1:2 and 2:1 and wherein the composition is comprised of between 225 and 275 mg of the alpha lipoic acid, between 2 and 6 mg of L-Dopa, and between 75 and 600 mg of the isoflavones in a single dosage form.

2. The composition of claim 1, wherein the isoflavones are at least 40% of the composition.

3. The composition of claim 1, wherein the isoflavones combination is a combination of isoflavones having R1=H and R2=H and R1=OH and R2=H.

4. The composition of claim 1, wherein the isoflavone combination is derived from red clover extract.

5. The composition of claim 1, wherein the L-Dopamine is derived from *Mucuna Pruriens*.

6. The composition of claim 1, wherein each of the alpha lipoic acid and L-Dopamine are combined in a single dosage form having a content of the isoflavones of between 100-500 mg.

7. The composition of claim 1, wherein each of the alpha lipoic acid, L-Dopamine and the isoflavones combination are combined in a single dosage form with a total isoflavone content comprised of combination of biochanin A and formononetin of at least 240 milligrams.

8. The composition of claim 1, wherein each of the alpha lipoic acid, L-Dopamine and the isoflavones are combined in a single dosage form having a total isoflavone content of at least 300 milligrams.

9. The composition of claim 1, wherein the L-form of dopamine is substantially free of a D-form of dopamine.

10. The composition of claim 1, wherein the alpha lipoic acid is at least 85% enriched for the (R) (+) enantiomer.

11. The composition of claim 10, wherein the alpha lipoic acid is a sodium salt thereof.

12. The composition of claim 1 is formed into a tablet or capsule.

* * * * *